US009255871B2

United States Patent
Mendoza De La Cruz et al.

(10) Patent No.: US 9,255,871 B2
(45) Date of Patent: Feb. 9, 2016

(54) MEASURING PROCESS OF DYNAMIC VISCOSITY OF HEAVY LIVE CRUDE FROM THE RESERVOIR PRESSURE UP TO ATMOSPHERIC PRESSURE, INCLUDING BUBBLE POINT PRESSURE, BASED ON AN ELECTROMAGNETIC VISCOMETER

(75) Inventors: José Luis Mendoza De La Cruz, Mexico City (MX); Roberto Carlos Ruiz Ortega, Mexico City (MX); Cecilia de los Ángeles Durán Valencia, Mexico City (MX); Simón López Ramírez, Mexico City (MX); Alfredo Ríos Reyes, Mexico City (MX); Oscar Orozco Caballero, Mexico City (MX); Luis Manuel Pizano Gallardo, Mexico City (MX)

(73) Assignee: Instituto Mexicano Del Petroleo, Mexico City (MX)

( * ) Notice: Subject to any disclaimer, the term of this patent is extended or adjusted under 35 U.S.C. 154(b) by 114 days.

(21) Appl. No.: 13/430,979

(22) Filed: Mar. 27, 2012

(65) Prior Publication Data
US 2013/0019663 A1   Jan. 24, 2013

(30) Foreign Application Priority Data
Mar. 28, 2011   (MX) .................... MX/a/2011/003287

(51) Int. Cl.
*G01N 11/00* (2006.01)
*G01N 11/08* (2006.01)
*G01N 11/10* (2006.01)

(52) U.S. Cl.
CPC ............... *G01N 11/08* (2013.01); *G01N 11/10* (2013.01); *G01N 2011/002* (2013.01)

(58) Field of Classification Search
CPC ..... G01N 11/08; G01N 11/10; G01N 11/105; G01N 11/12; G01N 2011/002
USPC ............ 73/54.01, 54.02, 54.23, 54.29, 54.31, 73/54.38
See application file for complete search history.

(56) References Cited

U.S. PATENT DOCUMENTS

| 2,209,755 A | 7/1940 | Beale |
| 2,348,732 A | 5/1944 | Fischer |

(Continued)

FOREIGN PATENT DOCUMENTS

| WO | WO2011/014202 | * | 3/2011 | ............. G01N 35/00 |

OTHER PUBLICATIONS

Barrufet, M.A. et al., Use of an automatic data quality control algorithm for crude oil viscosity data, Fluid Phase Equilibria 219 (2004) 113-121.

(Continued)

*Primary Examiner* — Peter Macchiarolo
*Assistant Examiner* — Natalie Huls
(74) *Attorney, Agent, or Firm* — Dickinson Wright PLLC

(57) ABSTRACT

The object of the present invention is to provide a process for experimental determination of heavy live crude oil dynamic viscosities reliable at a constant temperature (from ambient temperature to 463 K) and pressures from 68.9 MPa to the atmospheric pressure, including the dynamic viscosity at the bubble point pressure and by below of this point, based on a simple, reliable and accurate apparatus. The apparatus used in the present invention is based on an electromagnetic concept, only using a mobile element (piston) through a fluid at a constant force. The time required for the piston to travel a fixed distance is related exactly to the dynamic viscosity of the fluid contained in a measuring chamber. When the fluid contained in the inner part of the measuring chamber is more viscous, the piston displacement will be slower.

12 Claims, 6 Drawing Sheets

(56) References Cited

U.S. PATENT DOCUMENTS

| | | |
|---|---|---|
| 4,627,272 A | 12/1986 | Wright |
| 4,660,413 A | 4/1987 | Jones |
| 4,864,849 A | 9/1989 | Wright |
| 4,890,482 A * | 1/1990 | Maini .................... 73/54.14 |
| 5,025,656 A * | 6/1991 | Wright .................... 73/32 A |
| 5,612,493 A * | 3/1997 | Alexander ............. 73/152.55 |
| 6,584,831 B1 | 7/2003 | Kasameyer et al. |
| 6,792,798 B2 * | 9/2004 | Liang .................... 73/152.58 |
| 7,377,169 B2 * | 5/2008 | Myers et al. .............. 73/587 |
| 7,581,435 B2 * | 9/2009 | Pelletier ................. 73/54.02 |
| 7,595,876 B2 * | 9/2009 | DiFoggio ................. 356/328 |
| 7,804,296 B2 * | 9/2010 | Flaum et al. ............. 324/303 |
| 8,230,723 B2 * | 7/2012 | Moon et al. ............. 73/54.28 |
| 8,555,706 B2 * | 10/2013 | Kawamura et al. ...... 73/54.15 |
| 2008/0127717 A1 * | 6/2008 | Lesieur .................. 73/54.09 |
| 2010/0043538 A1 * | 2/2010 | Cheng et al. ............ 73/54.42 |
| 2010/0271019 A1 * | 10/2010 | Anand et al. ............. 324/303 |
| 2011/0093200 A1 * | 4/2011 | Hsu et al. .................. 702/8 |
| 2011/0185809 A1 * | 8/2011 | Guieze et al. ............. 73/32 R |

OTHER PUBLICATIONS

Dexheimer, D. et al. A modification of Pedersen's model for saturated crude oil viscosities using standard black oil PVT data, Fluid Phase Equilibria 183-184 (2001) 247-257.

Pedersen, K.S. et al., Properties of oils and natural gases, Gulf Publishing Company, Houston, Texas, vol. 5, 1989, 63-66.

Barrufet, M.A. et al., Experimental viscosities of heavy oil mixtures up to 450 K and high pressures using a mercury capillary viscometer, Journal of Petroleum Science & Engineering 40 (2003) 17-26.

* cited by examiner

MEASURING PROCESS OF DYNAMIC VISCOSITY OF HEAVY LIVE CRUDE FROM THE RESERVOIR PRESSURE UP TO ATMOSPHERIC PRESSURE, INCLUDING BUBBLE POINT PRESSURE, BASED ON AN ELECTROMAGNETIC VISCOMETER

TECHNICAL FIELD OF THE INVENTION

The invention refers to a process, based on a electromagnetic viscometer, for the experimental determination of dynamic viscosities of heavy live crude oils in the temperature range from 463 K to ambient temperature and pressures from 68.9 MPa up to atmospheric pressure, including the bubble point pressure as well as dynamic viscosities of liquid phase of the crude oil (no gas in solution) at each pressure stage under the bubble point pressure until reaching the atmospheric pressure.

BACKGROUND OF THE INVENTION

Reliable and accurate data of crude oil viscosity at different temperature and pressure conditions is required in the petroleum industry to calculate the fluids flow in the reservoir, for the design of production facilities and transportation pipelines on the surface. But all above, crude oil viscosity is essential to estimate crude oil recovery in a reservoir, either from natural depletion process (primary production) or from the recovery techniques such as water or gas injection processes (secondary or enhanced production method) (Barrufet, M. A. and Dexheimer, D., Use of an automatic data quality control algorithm for crude oil viscosity data, Fluid Phase Equilibria, 2004, 219, 113-121).

Live crude oil (fluid sample in a single phase extracted from the bottom of the well) largely depends on temperature, pressure, oil density, gas density, gas solubility, molecular structure sizes (asphaltenes and paraffins), and the composition of the hydrocarbon mixture (Barrufet and Dexheimer, 2004). Measuring fluids viscosity in a single-phase at high temperatures and high pressures is one of the most difficult activities in the petroleum industry, particularly due to the complexity of crude oil mixtures, and to the limitations of the appliances used to measure (Dexheimer, D., Jackson, C., Barrufet, M. A., A modification of Pedersen's model for saturated crude oil viscosities using standard black oil PVT data, Fluid Phase Equilibria, 2001, 183-184, 247-257).

There are few apparatuses designed and developed techniques to measure crude oil viscosity at reservoir temperature and pressure conditions. The most common techniques are: (1) a falling ball viscometer and (2) a capillary tube viscometer (Pedersen, K. S., Fredenslund, Aa., Thomassen, P., Properties of oils and natural gases, 1989, Gulf Publishing Company, Houston, Tex., 63-66). The first ones have a limitation in accuracy of viscosity and in the operation range of pressure and temperature conditions, besides they tend to an accumulation and deposition of matter, especially when using crude oils precipitating asphaltenes or paraffins. Besides, these viscometers have the disadvantage of not determine dynamic viscosity (or absolute), but they determine kinematic viscosity and require of the density value of fluid at the same measuring conditions in order to calculate dynamic viscosity. The second ones are difficult to use with different fluids due to cleaning problems, and a more prolonged time is required to reach the state of stabilization when fluids are changed; furthermore, this apparatus is extremely sensitive, especially at high pressures and it requires an accurate calibration of the differential pressure transducer, which is frequently a source of error (U.S. Pat. No. 4,660,413).

U.S. Pat. No. 4,890,482 refers to a method and apparatus to measure fluid viscosity. The apparatus described under this patent is related to a transitory flow capillary viscometer that measures viscosity of a highly viscous fluid. The operation principle consists on filling the capillary tube with the test fluid inducing a change in the pressure through the inlet and outlet of the capillary tube causing the fluid to flow. The resulting decrease in the pressure drop is a function of time, which is monitored to provide an indicative measure of fluid viscosity flowing through the capillary tube.

U.S. Pat. No. 4,660,413 refers to an apparatus and a method to determine the viscosity and density of a fluid by means of ascendant circulation of the fluid through a tube, which has a cup in the inner part, with a constant flow rate suspending the cup at equilibrium position. Then, a mass is added to the cup and a new flow rate of the fluid suspending the cup at equilibrium position is determined. Density and viscosity of the fluid are determined as a function of the two values of the fluid flow rate, and the apparatus characteristics.

U.S. Pat. No. 2,348,732 relates to a method and apparatus to determine fluids viscosity, as well as the oil density at dynamic conditions, such as the fluid was displaced through the pipeline.

U.S. Pat. No. 2,209,755 refers to an apparatus to measure fluids viscosity, such as lubricating oil, fuel oil, molasses, bitumen and substances with similar characteristics. This apparatus can also be applied to obtain an indication of the suspensions and emulsions consistency.

A viscometer of a capillary tube is described in literature to measure heavy oil viscosity and light hydrocarbon mixtures, at temperatures from ambient temperature to 450 K, and at pressures ranging from 0.1 MPa to 34 MPa (Barrufet, M. A., and Setiadarma, A., Experimental viscosities of heavy oil mixtures up to 450 K and high pressures using a mercury capillary viscometer, Journal of Petroleum Science & Engineering, 2003, 40, 17-26); the operation principle of the apparatus used in measurements consists on measuring the differential pressure of the laminar flow of a single-phase fluid along the capillary coils, and to convert it to viscosity by means of the Hagen-Poiseuille equation.

Another apparatus commonly used is the rotating viscometer measuring absolute viscosity by measuring the torque of a sample, and converting it to an absolute-viscosity value. However, the main limitation of this device is the pressure that can be reached in the system (Barrufet and Setiadarma, 2003). Rotational and vibrational viscometers, which can be an alternative to measure crude oil viscosity, are difficult to use at high temperatures and pressures (U.S. Pat. No. 4,890,482).

Despite counting on these apparatuses, most measurements carried out through these viscometers are not direct, that is, they do not measure dynamic viscosity directly, but they measure kinematic viscosity and require the density value, at the same temperature and pressure conditions, to calculate absolute viscosity (Barrufet and Setiadarma, 2003). In addition, a large amount of volume of the sample is required for the measuring test. Therefore an adequate process and an apparatus are required to determine highly viscous fluids viscosity at different temperature and pressure conditions.

The present invention is new due to consist on a process to measure dynamic viscosity of bottom-hole monophasic samples at a constant temperature and different pressures, as well as determine their thermodynamic behavior $(p,\mu)_T$ from the reservoir pressure ($\mu_o$ viscosity by above the bubble point pressure, $p_b$) to the atmospheric pressure ($\mu_{od}$ dead crude oil viscosity), including dynamic viscosities at the bubble point pressure ($\mu_{ob}$) and by below of this pressure ($\mu_b$); also is possible to determine the phases behavior L-V (saturation curve) of such fluids of reservoir. Unlike to the different methods described before, this method describes the dynamic viscosity directly of reservoir fluids at high temperature (up to 463 K) and high pressure (68.9 MPa) conditions at a wide range of viscosity (up to 10000 cP) and a 20-50 mL sample volume is required; essentially, the invention consists on a process to measure dynamic viscosity of heavy live crude oil by means of an apparatus containing a sensor based on a simple and novel technology: at a constant electromagnetic force. This apparatus uses a piston, calibrated in a determined range of viscosities, which is immersed in the crude oil to be analyzed. The piston displacement is resisted by viscous drag of the fluid, a characteristic used to obtain an accurate measurement of absolute viscosity. Time required by the piston to travel at a fixed distance is related to fluid dynamic viscosity confined in a measuring chamber. Therefore as the fluid in the measuring chamber is to be more viscous, the piston displacement will be slower.

BRIEF DESCRIPTION OF DRAWINGS OF THE INVENTION

The description of the invention is referred to the following drawings:

FIG. 1 shows a view of the cross-section of the mechanical part of the apparatus 1 used in the present invention. The apparatus consists on a measuring chamber 2 within which there is a piston 4 going back and forth by means of the alternate conduction of two electromagnetic coils 3 (A y B). One of the coils is placed in such a way that the magnetic field caused, when current flows through it, tends to drag the piston along the cannel. The second coil is positioned to drag the piston along the opposite channel.

FIG. 2 shows the schematic diagram to measure the dynamic viscosity of crude oil at different pressure and temperature conditions. A small amount of sample volume, contained in the high pressure stainless steel vessel, is required to perform the viscosity measuring at constant temperature; the temperature in the inner part of the measuring chamber is measured with a temperature sensor 17 connected to a digital indicator 23. A pressure transducer along with its digital indicator 16 is connected to the viscometer 18 to monitor pressure in the system. A RS-232 serial interface allows the viscometer 18 communication with a computer. To generate the pressure in the system, a positive displacement pump 1 is used, while for the temperature generation in the apparatus a circulating bath 22 is used.

FIG. 3 shows the typical behavior of a live crude oil when the pressure decreases at a constant temperature; in the pressure range delimited as R1 and R2, the crude oil is considered to be found in a single phase; in the region delimited as R2, it is considered as the region where the organic solids formation phenomenon would occur (especially asphaltenes), while R3 region is considered a multiple phase zone (crude oil, asphaltenes, gas). Generally, laboratory tests measure the viscosity behavior of crude oil at reservoir temperature, from the reservoir pressure up to the bubble pressure; once the gas is completely released from the crude oil (called dead crude oil), it is possible to measure viscosity at atmospheric pressure, and by means of correlations, estimate the viscosity value between the viscosity at the bubble pressure and the viscosity at atmospheric pressure. By the above additional data is required, which sometimes do not have, besides most of the correlations are not at all reliable.

DETAILED DESCRIPTION OF THE INVENTION

Figure 1:
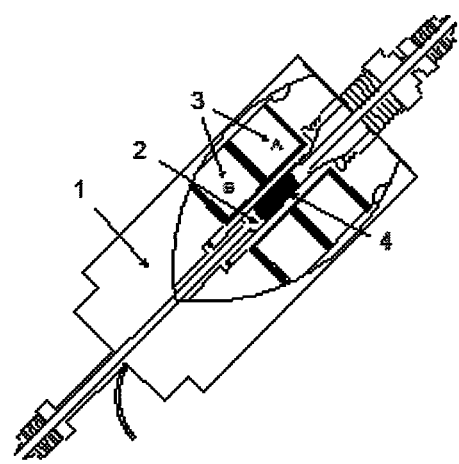

The invention refers to a measuring process of dynamic viscosity of heavy live crude oil at different temperatures (up to 463 K) and in the 68.9 MPa range up to atmospheric pressure, including the bubble pressure, based on an electromagnetic viscometer. The apparatus used in the present invention is particularly simple from the mechanical point of view, and the basic principle to determine viscosity is effective (U.S. Pat. Nos. 6,584,831 B1; 5,025,656; 4,864,849 and 4,627,272). The apparatus is accurate, reliable, easy to use and to maintenance. It is based on a simple, reliable electromagnetic principle using only a mobile element (piston containing ferromagnetic material), at a constant force, through a fluid. Time required for the piston to travel a fixed distance is accurately related to the dynamic viscosity of the fluid confined in a measuring chamber.

Measuring dynamic viscosity of a crude oil sample, extracted from the bottom of a well, is generally carried out at reservoir temperature. Once the crude oil sample is loaded to the measuring system of viscosity (stage A) and stabilized, at reservoir temperature and pressure, viscosity readings are recorded, as well as the temperature values and study pressure. After a measuring time of the viscosity values, at the corresponding temperature and pressure, the pressure to measure viscosity value decreases, at that new pressure condition; as a result from pressure decrease (decrements from 3.4 or 6.9 MPa from the reservoir pressure up to a pressure value near the bubble pressure), temperature in the system is altered. After stabilizing the study temperature again, the viscosity value is measured for that pressure. Near the bubble pressure, the decrement in pressure is much less (0.7 to 1.4 MPa). This procedure is continued until there is a slope change in the viscosity behavior as pressure decreases (stage B); the point immediately before the change of the viscosity slope is considered as the bubble point (formation of the first gas bubble) (stage C). When reaching the pressure bubble, the de-pressurization process of the system continues and at each pressure stage the viscosity value is recorded to analyze the precipitation and flocculation effect of asphaltenes in viscosity behavior.

When reaching the point where the gas phase forms and multiple phases coexist in the system (considering the formation of asphaltenes), the system pressure is decreased between 3.4 and 6.9 MPa from the value measured of the bubble pressure. Then, the apparatus is placed vertically to lead to the formation of a gas cap. The system is held at this pressure for several hours. Later, the system pressure is increased (above the bubble pressure value) and the formed gas cap is removed, holding the measured bubble pressure value (stage D). When the gas cap has been completely removed, making sure that the crude oil viscosity value is higher than the viscosity in the measured bubble point, the pressure of the system is again increased (process of re-pressurization) (stage E). Once the temperature is reset, and the pressure in the system does not change, the viscosity of the new crude oil is measured. Afterwards the system pressure is decreased again; set up small pressure decrements and pressure is measured until detecting a new slope change in the viscosity behavior. The point immediately before the phase transition corresponds to dynamic viscosity by below the bubble point pressure ($\mu_b$) (stage F). To determine several viscosity values below the bubble pressure, it is necessary to repeat the process described previously until reaching the atmospheric pressure in the system (stage G).

It is important to mention that the viscosity value, at atmospheric pressure (no gas in solution) measured by this process, will be less compared to the viscosity value of the same crude oil measured after a few days.

Example

Figure 2:
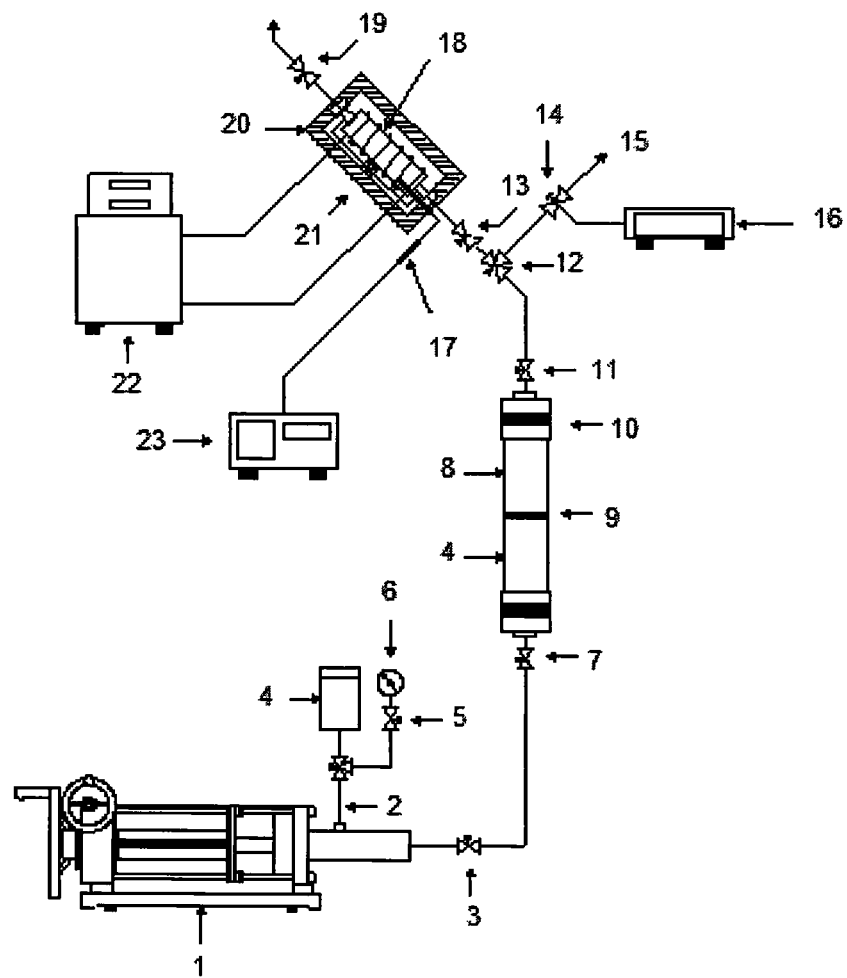
Figure 3:
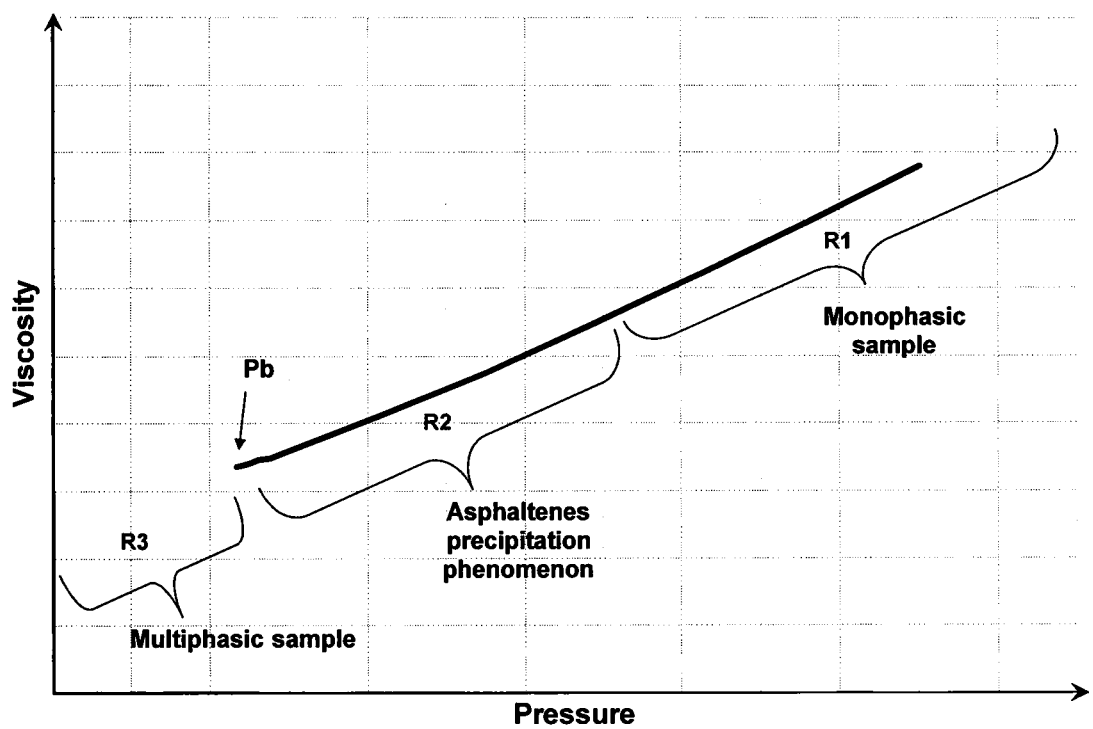

Before include an example, it is important to mention that in order to guarantee our determinations of dynamic viscosity are reliable, we previously calibrated the piston to be used, as well as the pressure transducer and temperature sensor of the system. The calibration and verification of the piston were carried out with the following standards S20, S3, S6 (supplied by Cannon Instrument Company, ASTM D2162) and involves the measurement of a standard fluid identifiable at a stable temperature and adjust the calibration parameters corresponding to the piston selected to reproduce the dynamic viscosity (with an average standard deviation of ±1.0%) corresponding to the known value of such calibration standards at the required temperature. The following example demonstrates the process performance, and the apparatus herein described for the dynamic viscosity experimental determination of a heavy live crude oil, at different pressures and at constant temperature (FIG. 2).

Figure 4:
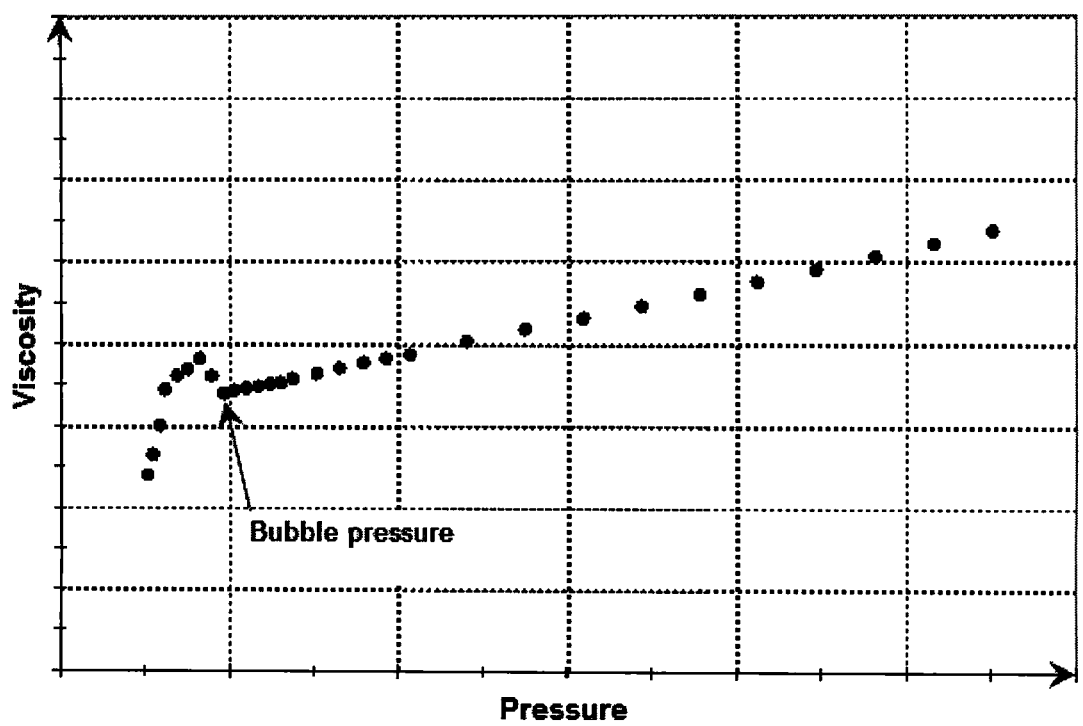
FIG. 4 shows a viscosity isotherm of a heavy live crude oil from the reservoir pressure up to the bubble pressure, including the typical behavior of viscosity below this point, that is, when several phases coexist.
Figure 5:
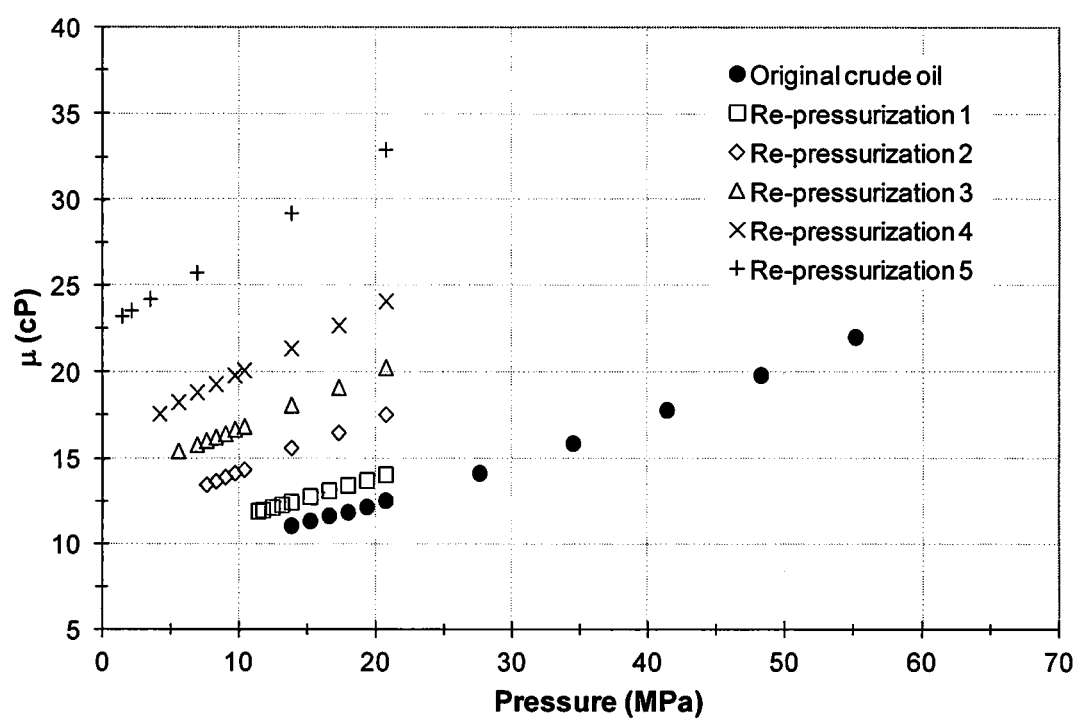
FIG. 5 shows the process of the present invention for measuring heavy live crude oil viscosity from the reservoir pressure up to the bubble pressure, as well as the different extraction stages of released gas and the system re-pressurization to measure only the liquid viscosity after the first gas bubble has formed until reaching the atmospheric pressure.
Figure 6:
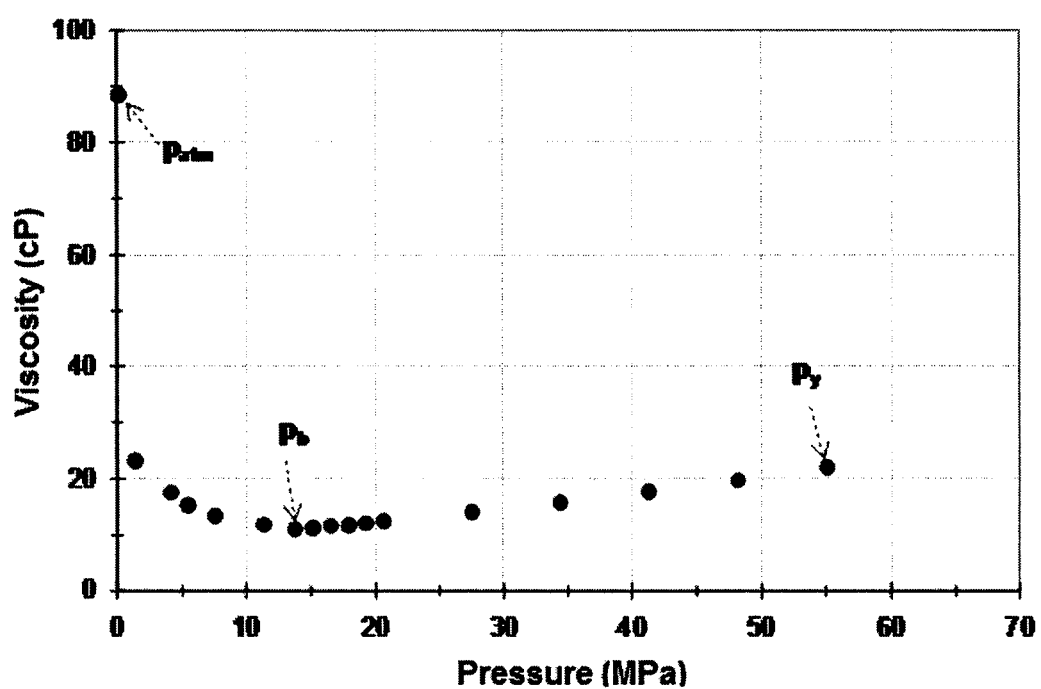
FIG. 6 shows the complete viscosity isotherm from a heavy live crude oil, object of the present invention, from the reservoir pressure up to the atmospheric pressure, including dynamic viscosities by below of the bubble pressure.

The simple of heavy live crude oil 8 is transferred, at reservoir conditions, to a high pressure stainless steel vessel 10 and connected to the measuring circuit through valves 7 and 11. The high pressure stainless steel vessel 10 has in its inner part, a piston 9 floating freely through the stainless steel vessel 10, separating the crude oil sample 8 from the pressurization fluid 4. To keep a homogeneous temperature in the measuring system, the high pressure stainless steel vessel 10 is heated by means of a heating resistance. The stainless steel lines, integrating the measuring circuit, are also heated by means of heating tapes. Through the circulating bath 22 the temperature in the system is set up. The temperature in the apparatus is measured through a temperature detector 17 connected to a digital indicator 23. The system pressure is generated and controlled by a positive displacement pump 1 using a mineral oil 4 as pressurization fluid. The pressure in the system is monitored by means of a pressure transducer, which is connected to a pressure digital indicator 16. When the temperature in the apparatus 18 is near the measuring temperature, the apparatus 18 is placed vertically and connected to a vacuum pump 15 through valve 14. Valves 12, 13, 14 and 21 must be open during the vacuum process, while valves 11 and 19 must remain closed. Evacuate the measuring circuit up to reach an appropriate vacuum process (generally, after 20 minutes approximately), shut valves 14, 12, 13 and 21. Set up the reservoir pressure in the positive displacement pump 1, and slowly open valves 3, 7, 11 12, 13 and 21. Valve 2 must remain shut, while valve 5 must be open. To make sure that the crude oil sample is in single phase, purge a small amount of crude oil volume through valves 14 and 19. Slowly shut valve 21 and place the apparatus 18 in measuring position (45° C.). When the crude oil sample is stabilized at a temperature and pressure, record the dynamic viscosity values as well as the pressure and pressure values. By means of the positive displacement pump 1, decrease the pressure in the system (decrements can be from 6.9 or 3.4 MPa, from the established pressure up to a pressure value near the bubble pressure). When the analysis temperature is again stabilized, record the viscosity value for such pressure. Near the bubble pressure, the decrement in pressure is much less (it can be from 0.7 to 1.4 MPa). This procedure is continued until there is a slope change in the viscosity behavior as pressure decreases (as shown in FIG. 4); the point immediately before the slope change of viscosity is considered as the bubble point pressure ($p_b$, formation of the first gas bubble). When reaching the point where the gas phase forms and in the system multi-phase coexist (considering the formation of asphaltenes), the pressure of the system is decreased between 3.4 and 6.9 MPa of the value measured from the bubble pressure. Then, the apparatus 18 is placed vertically leading to the formation of a gas cap. The system is held for several hours at this pressure. The system pressure is later increase (by above the bubble pressure value) and the gas cap formed is removed by valve 19, keeping the value of the bubble pressure measured. A plastic line is connected through valve 19 to remove the gas cap released by the expansion process, and collected in a stainless steel vessel. The purpose of using a plastic line is to observe and guarantee that only the gas phase is extracted from the system. When the gas cap has been completely removed, making sure that the crude oil viscosity value is higher than the viscosity in the measured bubble point pressure, the pressure of the system is again increased at least double the value of the bubble pressure. To guarantee that in the measuring chamber 2 (FIG. 1) is the crude oil in the liquid phase, a small amount of the sample volume is purged through valve 19. Once the temperature is restored and the system pressure does not change, viscosity of the crude oil is measured (squared symbols in FIG. 5). Then, decrease again the pressure in the system; set up small pressure drops and measure pressure until finding a new slope change in the viscosity behavior. The point immediately before the slope change (phase transition) represents the crude oil viscosity by below the saturation pressure. To determine several viscosity values by below the bubble pressure, it is necessary to repeat the described process herein until reaching the atmospheric pressure in the system ($p_{atm}$). For this heavy crude oil particularly, several extraction stages of the gas phase were carried out as well as several re-pressurization and de-pressurization processes of crude oil (rhombus, triangle, cross, and the rest of the symbols shown in FIG. 5) to measure the viscosity values by below the saturation pressure until reaching the atmospheric pressure (FIG. 6).

Having described our invention enough, we consider it as an innovation and therefore, we reclaim it as our exclusive property the content in the following claims:

1. A process for determining dynamic viscosities of monophasic samples extracted from a crude oil well comprising:
   measuring the viscosity of a 20 to 50 mL crude oil sample at a first temperature up to 463 K and a first pressure greater than the atmospheric pressure;
   decrementally reducing the pressure from the first pressure to a second pressure, subsequently stabilizing the sample at the first temperature, and thereafter measuring the viscosity at each pressure decrement and at the first temperature to determine a bubble point pressure and the dynamic viscosity at the bubble point pressure of the sample;

measuring the bubble point pressure $p_b$;

extracting a gas cap from the sample to create a new sample;

re-pressurizing the new sample above the bubble point pressure $p_b$ of the sample after extracting the gas cap; and decreasing the pressure and measuring the viscosity $\mu_b$ from below the bubble point pressure to a phase transition.

2. A process as defined in claim 1 comprising:

loading the sample into a viscosity measuring system;

measuring the viscosity from the viscosity $\mu_o$ at the reservoir pressure to the viscosity $\mu_{ob}$ at the bubble point pressure; and measuring the viscosity $\mu_{od}$ at atmospheric pressure.

3. A process as defined in claim 2, further comprising isothermally and isobarically transferring the crude oil sample into the viscosity measuring system.

4. A process as defined in claim 2 comprising reducing the pressure below the bubble point pressure to form the gas cap.

5. A process as defined in claim 2 wherein at the atmospheric pressure all gas is extracted from the sample.

6. A process as defined in claim 2, wherein the viscosity measuring system comprises, a measuring chamber having a piston, a pressure transducer having a digital indicator operable with the measuring chamber, a circulating bath operable with the measuring chamber, the measuring chamber including a high pressure stainless steel vessel, and the piston including a stainless steel floating piston, ⅛ in. inner diameter high pressure stainless steel tubing operable with the measuring chamber, a high pressure stainless steel valve operable with the measuring chamber to control crude oil flow, a computer for recording and storing of data from the measuring chamber, a positive displacement pump and pressurization fluid to generate and control system pressure in the measuring chamber, a temperature sensor welded to the lower part of the measuring chamber, a vacuum pump operable with the measuring chamber, ⅛ in. inner diameter plastic tubing operable with the measuring chamber, and a temperature controller operable with the measuring chamber.

7. A process for determining the dynamic viscosity of a crude oil in a well comprising;

placing a 20 to 50 mL sample of crude oil in a measuring chamber at a first temperature and a first pressure;

decrementally reducing the pressure from the first pressure, subsequently stabilizing the sample at the first temperature, and thereafter measuring the viscosity of the sample at the first temperature and the reduced pressures;

identifying a bubble point viscosity and bubble point pressure of the sample;

decreasing the pressure from the bubble point pressure and placing the measuring chamber in a vertical orientation to form a gas cap;

removing the gas cap by increasing the pressure to a predetermined amount to create a new sample; and raising the pressure of the new sample to a second pressure and subsequently stabilizing the temperature at the first temperature, wherein the second pressure is at least double the bubble point pressure of the sample.

8. The process of claim 7, further comprising decrementally reducing the pressure from the second pressure, subsequently stabilizing the sample at the first temperature, and thereafter measuring the viscosity of the sample at the first temperature and the reduced pressures.

9. The process of claim 8, further comprising repeating the process until all gas is removed from the sample.

10. The process of claim 7, wherein the first pressure is the reservoir pressure and the first temperature is the reservoir temperature.

11. A process for determining the dynamic viscosity of a crude oil in a well comprising;

obtaining a 20 to 50 mL sample of live crude oil;

isothermally and isobarically transferring the crude oil sample into a viscosity measuring device;

stabilizing the sample at a reservoir temperature and reservoir pressure;

measuring the viscosity of the sample at the reservoir pressure;

reducing the pressure from the reservoir pressure in a series of steps, subsequently stabilizing the sample at the reservoir temperature, and thereafter measuring the viscosity at each step at the reservoir temperature until a change in slope of the viscosity measurements is detected to determine the bubble point pressure;

further decrease the pressure from the bubble point pressure;

orient the viscosity measuring device to form a first gas cap;

removing the first gas cap to create a first new sample;

raising the pressure of the first new sample to a second pressure at least double the bubble point pressure of the sample and subsequently stabilizing the temperature at the reservoir temperature;

reducing the pressure from the second pressure in a series of steps, subsequently stabilizing the sample at the reservoir temperature, and thereafter measuring the viscosity at each step at the reservoir temperature;

orient the viscosity measuring device to form a second gas cap;

removing the second gas cap to create a second new sample;

continuing to increase the pressure, decrease the pressure in steps, form a gas cap, and removing the formed gas cap until no gas is left in the sample.

12. The process of claim 11, wherein the sample is live heavy crude oil.

* * * * *